United States Patent [19]

Ryder

[11] Patent Number: 4,638,807
[45] Date of Patent: Jan. 27, 1987

[54] HEADBAND ELECTRODE SYSTEM
[75] Inventor: Francis E. Ryder, Arab, Ala.
[73] Assignee: Ryder International Corporation, Arab, Ala.
[21] Appl. No.: 770,150
[22] Filed: Aug. 27, 1985
[51] Int. Cl.$^4$ .............................................. A61B 5/04
[52] U.S. Cl. ................................................... 128/644
[58] Field of Search .............. 128/17, 20, 303 A, 380, 128/639, 644, 731, 790, 791, 792, 799, 641; 24/587, 588

[56] References Cited

U.S. PATENT DOCUMENTS

| | | | |
|---|---|---|---|
| 910,362 | 1/1909 | Dieudonne | 128/380 |
| 2,670,731 | 3/1954 | Zoll et al. | 128/20 |
| 3,659,614 | 5/1972 | Jankelson | 128/791 |
| 3,735,753 | 5/1973 | Pisarski | 128/644 |
| 3,841,312 | 10/1974 | Corasanti | 128/641 |
| 3,896,790 | 7/1975 | Dikmen | 128/644 |
| 4,029,086 | 6/1977 | Corasanti | 128/641 |
| 4,088,133 | 5/1978 | Twentier | 128/644 |
| 4,126,126 | 11/1978 | Bare et al. | 128/639 |
| 4,233,987 | 11/1980 | Feingold | 128/639 |

Primary Examiner—Lee S. Cohen
Assistant Examiner—Randy Citrin
Attorney, Agent, or Firm—Trexler, Bushnell & Wolters, Ltd.

[57] ABSTRACT

A headband electrode system comprises an elongate flexible band, a center electrode coupled to a central portion of the band and a pair of temporal electrodes coupled with the band, one to either side of the center electrode. A pivotal mounting arrangement is provided for each of the temporal electrodes for pivotal movement relative to the band for positioning the temporal electrodes for predetermined placement relative to the center electrode.

16 Claims, 8 Drawing Figures

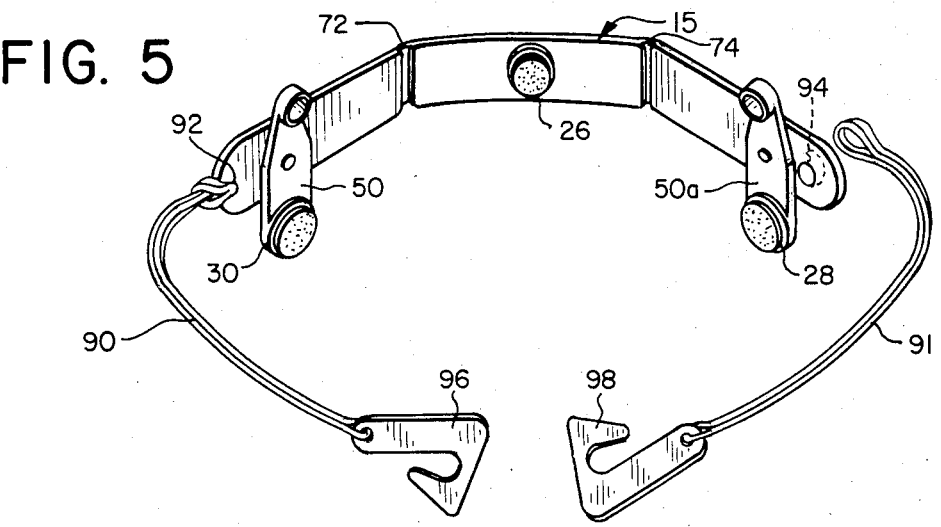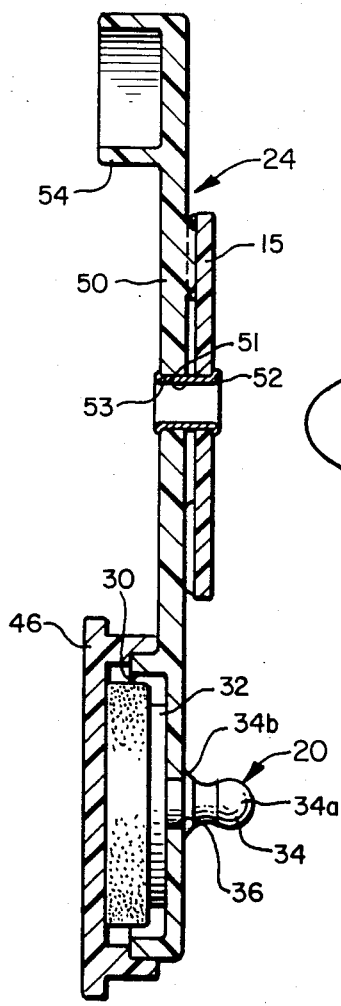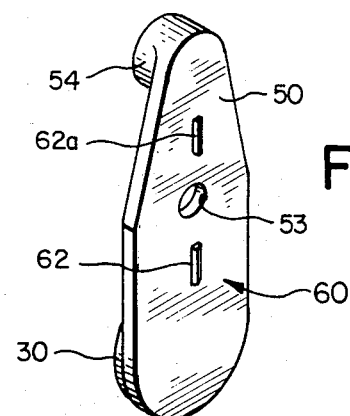

HEADBAND ELECTRODE SYSTEM

BACKGROUND OF THE INVENTION

This invention is directed generally to the field of medical testing or monitoring electrodes and more particularly to a headband-carried electrode system particularly suited for non-invasive alcohol/drug analysis.

Electrodes of various types are placed on the external surfaces of the body for purposes of performing a number of medical tests or analysis procedures. The present invention relates to a novel system or apparatus for placing a number of electrodes about the forehead region of the body to accomplish such medical testing, as for example measuring the corneo-retinal potential of a subject.

A body of data has been empirically developed relating the corneo-retinal potential to the presence in the body of varying levels of controlled substances. More particularly, it has been proposed to utilize this body of data and such measurements to assess the presence in the body of alcohol and/or a number of frequently abused substances, such as barbiturates, tranquilizers, opiates, and hallucinogens.

That is to say, each substance will produce a particular type of waveform which is unique to that substance. Hence, the waveform obtained from a suspected individual may be essentially "compared" to the known waveforms from the empirical data to determine whether or not the subject is under the influence or is otherwise impaired by a drug and/or alcohol. Additionally, the configuration of the waveform will identify the particular substance involved be it alcohol, amphetamines, barbiturates, tranquilizers, opiates, cocaine, or hallucinogens including PCP and marijuana.

Such testing has heretofore been carried out using three electrodes attached to the forehead of the subject. The first or central electrode is substantially centrally placed upon the forehead. An additional two side or temporal electrodes are placed at predetermined positions relative to the temporal lobes of the forehead of the subject. The proper placement of the electrodes is believed important in obtaining reliable results. Moreover, it has been found that there is a wide range of variance among individuals as to the proper locations of the temporal electrodes relative to the forehead and relative to the center electrode. For example, it has been found that both the vertical and the lateral distances between the temporal electrodes and the center forehead electrode (the vertical distance being the difference in elevation) tend to decrease with decreasing head size. Conversely, these distances tend to increase with increasing head size of the subject.

OBJECTS AND SUMMARY OF THE INVENTION

Accordingly, it is a general object of the invention to provide a novel and improved headband electrode system for mounting a center electrode and a pair of temporal electrodes on a single headband for simplifying the attachment of electrodes to a subject for testing.

A more particular object is to provide a headband electrode system in accordance with the foregoing object wherein the relative positions of the electrodes are readily adjustable to accommodate subjects whose head sizes vary over a relatively wide range.

A related object is to provide a headband electrode system in accordance with the foregoing objects which is relatively simple and inexpensive in its design and manufacture, preferably so as to be disposable after use, and yet highly reliable in use.

Briefly, and in accordance with the foregoing objects, a headband electrode system according to the invention comprises an elongate flexible band; a center electrode coupled to a central portion of said band; a pair of temporal electrodes coupled with said band, one to either side of said center electrode; and pivotal mounting means for mounting each of said temporal electrodes for pivotal movement relative to said band for positioning said temporal electrodes for predetermined placement relative to center electrode.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawings, in which like reference numerals identify like elements, and in which:

FIG. 5 is a rear perspective view, similar to FIG. 4, illustrating an alternate form of band or strap for affixing the headband electrode system to the head of the subject;

FIG. 6 is an enlarged sectional view taken generally in the plane of the line 6—6 of FIG. 2;

FIG. 7 is an enlarged rear perspective view of an elongate arm element of the headband electrode system of the invention; and FIG. 8 is an exploded perspective view illustrating details of the assembly of the element shown in FIG. 7 with other members and its pivotal mounting to the band portion of the headband electrode system of the invention.

DETAILED DESCRIPTION OF THE ILLUSTRATED EMBODIMENT

Figure 1:
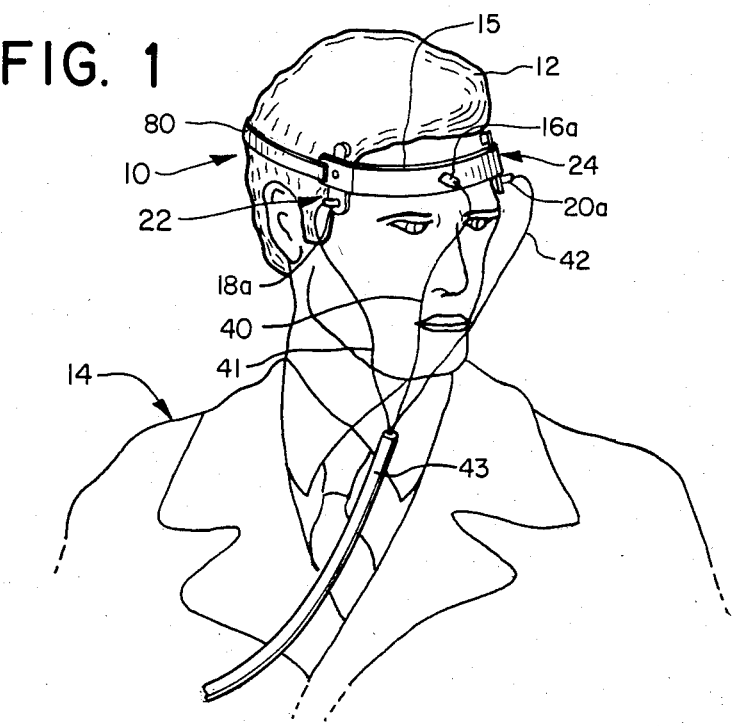
FIG. 1 is a perspective view illustrating a headband electrode system in accordance with the invention in use for measuring the corneo-retinal potential of a subject.

Referring now to the drawings, a headband electrode system in accordance with the invention is designated generally by the reference numeral 10. In FIG. 1, the headband electrode system 10 is illustrated in use, attached to the head 12 of a patient or a subject 14. Preferably, the system is utilized for measuring the corneo-retinal potential of the subject or patient 14. As discussed above, this corneo-retinal potential measure may be related by emperically developed data to the presence in the body of tbe subject or patient 14 of various levels of controlled substances. More particularly, this body of data and the measurements obtained may be utilized to assess the presence in the body of the patent or subject 14 of alcohol and/or a number of frequently abused substances.

Figure 3:
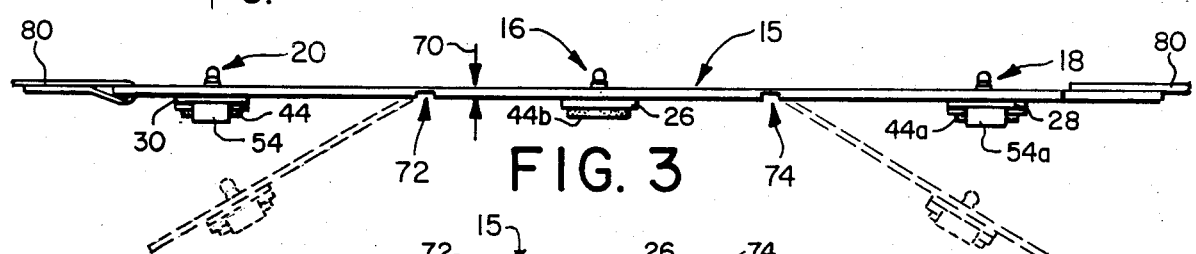
FIG. 3 is a top plan view of the headband electrode system of FIG. 2.
Figure 4:
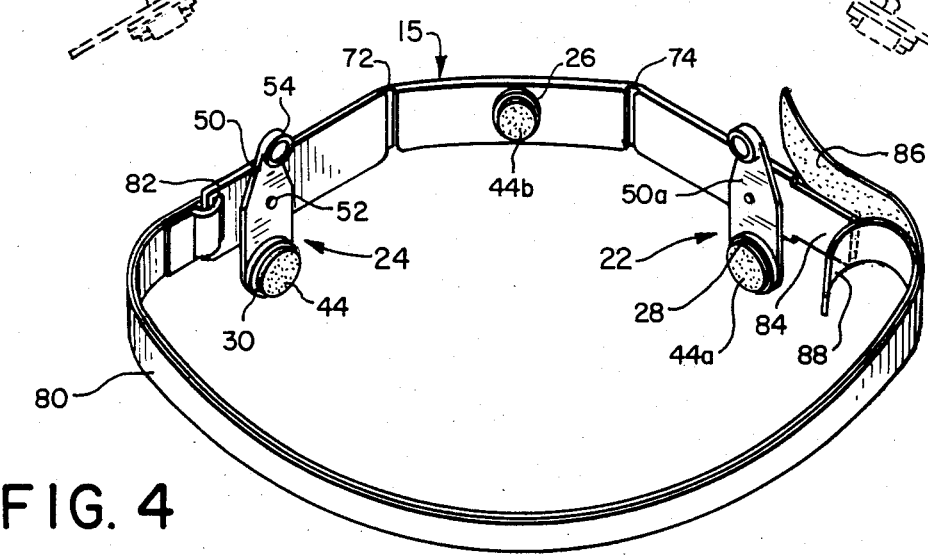
FIG. 4 is a rear perspective view of the headband electrode system of FIG. 2.

The above-described measurement of corneo-retinal potential is carried out by placing three electrodes 16, 18 and 20 (See FIG. 3) in contact with the head of the subject. In FIG. 1, three mating electrode connectors 16a, 18a and 20a electrically coupled with the electrodes 16, 18, 20 and with leads 40, 41, 42 of a cable 43 which connects to a monitoring device (not shown). The headband electrode system 10 also includes an elongate flexible band 15 which mounts electrodes 16, 18 and 20.

The first or central electrode 16 is to be placed or held substantially centrally upon the forehead of the subject. The other two electrodes 18, 20 are side or temporal electrodes to be placed at predetermined positions relative to the temporal lobes of the subject. In this regard, it has been found that there is a wide range of variance among individuals as to the locations of the temporal lobes, and hence of the temporal electrodes 16, 18, relative to the center of the forehead and location of the center electrode 16. For example, it has been found that both the vertical and lateral distances between the desired positions of each of the temporal electrodes 18, 20 and of the center electrode 16 decrease with decreasing head size of the subject. Conversely, these distances between the desired positions or placements of the electrodes relative to one another tend to increase with increasing head size.

In order to accomplish the desired placements of temporal electrodes 18, 20 relative to center electrode 16, while also accommodating a broad range of variations in head sizes of subjects which affect these desired relative placements thereof, pivotal mounting means designated generally 22 and 24 are provided. These pivotal mounting means or assemblies 22 and 24 are advantageously arranged for mounting the temporal electrodes 18, 20 for pivotal movement relative to the elongate, flexible band 15 to thereby position the temporal electrodes, as desired, in a predetermined placement relative to the temporal lobes of the subject and relative to the placement of the center electrode 16.

Referring now also to the remaining drawings, the system 10 includes electrode-receiving means, each comprising a hollow, cup-like structure or member 26, 28 and 30 for respectively receiving the electrodes 16, 18 and 20 therein. In this regard, the electrodes mounted within each of the cup-like receiving means are substantially identical, whereby only one such electrode 20 will be described in detail.

As best viewed in FIGS. 6 and 7, the electrode 20 comprises a generally flat, disc-like electrode portion 32 and a connector portion 34, preferably having a snap-like configuration projecting therefrom. Cooperatively, an inner bottom wall of the cup-like member 30 has a through aperture 36 for receiving the snap-like connector portion 34 projecting therethrough for snappingly engaging a mating connector. In this regard, the snap-like portion 34 preferably includes a first or leading snap surface 34a for engaging a mating connector 20a formed at the end of the lead or conductor member 42 of a cable 43 (see FIG. 1).

A second, following snap surface 34b preferably comprises a generally annular, flared skirt portion following the first snap surface 34a for resiliently deforming to pass through aperture 36 and thereafter resiliently returning to the shape illustrated in FIG. 6 for snappingly engaging the rear surface of cup-like member 30 about the through aperture 36. In this regard, it is noted that the center electrode 16, as well as each of the temporal electrodes 18 and 20 are substantially concentrically located within the generally circular or cylindrical space defined by the electrode receiving cup-like members 26, 28 and 30.

Each electrode is also provided with a gel-filled pad 44, 44a, 44b preferably of a circular disc-like configuration and complementary with the interior dimension of cup-like portion or member 30 for being received therein overlying the disc-like electrode portion 32. This gel-filled pad is filled with a suitable electrolyte gel to promote electrically conductive contact between the skin of the patient or subject 14 and the respective electrodes 16, 18 and 20. As best viewed in FIGS. 6 and 7, each of the electrode receiving means may further include a removable, cup-like cover member 46 which snappingly engages about the outer surface or rim of cup-like member or portion 30. This removable cover 46 maintains the gel-filled pad 44 and electrode 20 in a clean or uncontaminated condition, and further facilitates the retention of moisture and resultant spongy or resilient character of the pad 44.

As best viewed in FIGS. 6 and 7, each of the pivotal mounting means or assemblies 22, 24 comprises an elongate arm means or member 50 pivotally mounted to the headband. Preferably, a rivet 52 extending through aligned through apertures 51 and 53 of the headband and arm 50 is used to effect this pivotal mounting. In this regard, the pivotal mounting means or mounting assemblies 22 and 24 are substantially identical, whereby only the mounting assembly 24 will be fully described herein. Elongate arm member 50 will be seen to be pivotally mounted by rivet 52 substantially at a central portion thereof to the flexible band 15.

The electrode receiving means or cup-like member 30 is formed at one end of the arm 50 for receiving the temporal electrode 20 as previously described. Moreover, a gripping means or gripping member or projection 54 is provided at the opposite end of the elongate arm 50 for manually pivoting the arm to place the electrode in the desired or predetermined position relative to the temporal lobes of the subject 14 and also relative to center electrode 16. In this regard, it will be seen that the pivotal mounting means or mounting structures 28 and 30 are located on the flexible band 15 to either side of the center electrode 16 and substantially equally distant therefrom.

Figure 2:
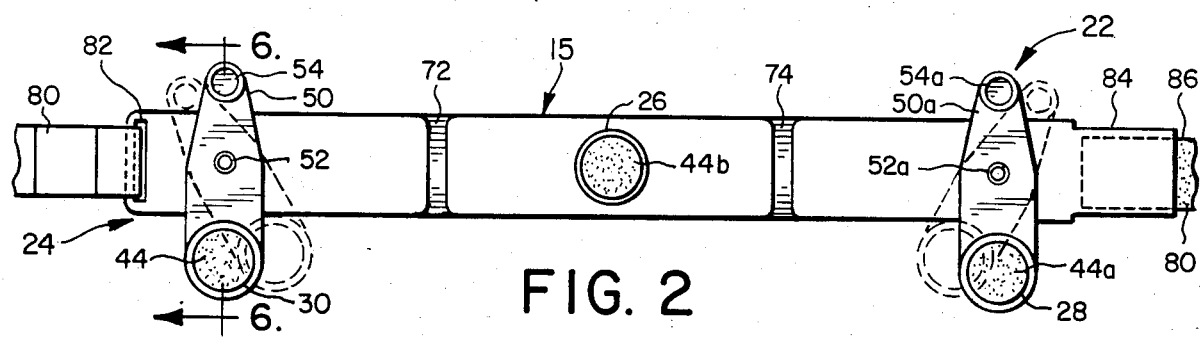
FIG. 2 is an enlarged rear elevation illustrating the headband electrode system of FIG. 1 in additional detail.

Advantageously, and as generally indicated in phantom line in FIG. 2, this pivotal mounting of the temporal electrodes 18 and 20 permits adjustment of the positions thereof to conform to the variations in head sizes among subjects or patients as previously noted. That is, it will be noted that as the respective pivotally mounted arms 50 and 50a (like reference numerals with suffix a being used with respect to mounting assembly 22) are pivoted as shown in phantom line in FIG. 2, the electrodes thereof move not only laterally closer to center electrode 16 but also move relatively upwardly so as to decrease the relative vertical distance or spacing thereof from electrode 16.

Hence, a range of relative positions of the electrodes is provided for accommodating a relatively large range of head sizes. That is, with mounting assemblies 22 and 24 in the position shown in full line in FIG. 2 a relatively large head size is accommodated, whereas with the assemblies 22 and 24 pivoted in the directions indicated in phantom line in FIG. 2 relatively smaller head sizes are accommodated. Hence, the described pivotal motion of arms 50, 50a accommodates desired electrode placements as noted by simultaneously adjusting both the lateral spacing and the vertical spacing between the respective temporal electrodes and the center electrode so as to generally increase with increasing head size and decrease with decreasing head size.

In accordance with a preferred feature of the invention, detent means, designated generally by reference numeral 60 are provided for defining a plurality of detent positions of each of the pivotal mounting means or structures 22, 24 relative to the band 15. In this regard, each of the pivotal mounting means and in particular, each of the rivets 52, defines a pivot center, and the elongate arm 50 and band 15 include substantially flat, facing surfaces. Accordingly, the detent means 60 comprises at least one raised rib on one of the facing surfaces of the band 15 and arm 50 lying generally along a radius of the pivot center, and a plurality of spaced apart ribs 64 on the other facing surface. These latter ribs are arranged in a generally arcuate configuration, for sequential, detent-like or clicking engagement with the first rib 62.

In the illustrated embodiment, the first rib 62 comprises a pair of similar ribs 62, 62a formed generally along a common diameter of the pivot center, and on the flat undersurface of the pivot arm member 50. Accordingly, the second ribs 64 comprise two similar groups of arcuately arranged ribs 64, 64a, these groups being substantially symmetrically formed with respect to each other and with respect to the pivot center. Each of these groups of ribs 64, 64a comprises a plurality of similar, spaced apart raised ribs, each of these ribs defining a radius of the pivot center. Preferably, each of the ribs 62, 62a as well as each rib of the groups of ribs 64 and 64a comprises a relatively thin, elongate raised member, preferably having generally tapered or rounded lateral edges, to facilate the sliding, detented motion therebetween.

In accordance with a further preferred feature of the invention, the band 15 comprises a relatively thin, flat member having a first predetermined thickness as indicated at reference numeral 70 (See FIG. 3) over a major portion of the length thereof. To facilitate flexing to conform to the head of the subject or patient 14, the band has at least one, and preferably two cross-sectional regions 72, 74 of decreased thickness. As best viewed in FIG. 3, these regions 72 and 74 comprise relatively narrow areas extending transversely across the band 15, one to either side of the center electrode 16 thereon and substantially equally distant from the center electrode. The flexing action of the band 15 about regions 72, 74 is illustrated in phantom line in FIG. 3.

Preferably, an additional strap or flexible strap means 80 is provided for affixing the band 15 to the head of the subject so as to position the center electrode substantially centrally upon the forehead of the subject. Preferably, this strap or strap means is adjustable to a desired effective length intermediate the respective ends of the band 15 for accommodating a range of head sizes.

In the embodiment illustrated in FIGS. 1 through 4, the strap means comprises a relatively thin, flat elongate strip of tearable tape like material, whereby the effective length thereof may be adjusted by tearing, cutting or otherwise severing at the point desired. Moreover, this material has an adhesive surface 86 for adhesively gripping the opposite ends of the band 15. In the embodiment illustrated, one end of the band 15 is provided with an elongate transverse slot 82 for receiving one end of the elongate tape member 80 looped therearound and adhesively affixed to itself. The opposite end of the band 15 has a tab-like extension 84 for receiving an opposite end of the tape member adhesively affixed thereto, once the length thereof is adjusted as desired. This tape 80, as mentioned, has a selectively exposeable adhesive surface 86. To this end, the tape may be a double-layered type, having a peelable layer 88 overlying the adhesive surface 86, thus rendering the adhesive surface selectively exposeable.

In the embodiment illustrated in FIG. 5, the strap means or member comprises a pair of elongate bands 90, 91 of elastomeric material each of which may be in the nature of a "rubber band" or a similar flexible loop member. To accommodate these bands, one end of the headband 15 is provided with a through aperture 92 such that an end of the loop or band 90 may be passed therethrough and looped around or over itself. The opposite end of headband 15 includes a projecting post member 94 having an enlarged head to receive one end of the flexible band 91 looped thereabout. Both ends of the headband 15 may be configured the same way, using either an aperture or post as desired.

The opposite ends of bands 90 and 91 are provided with similar, but oppositely disposed hooks or hook-like members 96, 98. These hooks 96, 98 have through apertures for receiving the other end of each band looped therethrough in the same fashion as band 90 at aperture 92. The hooks are configured for releasable interengagement for releasably securing bands 90, 91 and headband 15 around the head of the subject. A single elastic band such as band 90 may also be utilized coupled between opposite ends of headband 15 if desired.

It will be noted that each of the mounting assemblies 22, 24 preferably comprises a one-piece integrally formed member, preferably of a flexible material. Similarly, the elongate flexible band or headband 15 and electrode receiving means or cup-like portion 26 thereof preferably comprises a one-piece integrally formed member of a flexible material.

While particular embodiments of the invention have been shown and described in detail, it will be obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiment and specific construction described herein but should be defined by the appended claims and equivalents thereof. Accordingly, the aim in the appended claims is to cover all such changes and modifications as fall within the true spirit and scope of the invention.

The invention is claimed as follows:

1. A headband electrode system comprising: an elongate flexible band; a center electrode mounted upon said band at a central portion of said band at a first elevation relative to said band; a pair of temporal electrodes; a pair of arm members each carrying one of said temporal electrodes, said arm members extending from said band to dispose the temporal electrodes at a second elevation relative to the band such that said temporal electrodes are below said center electrode, and pivotal mounting means connecting the arm members to the band, such that said arm members are pivotally mounted to the band, one to either side of the center electrode for mounting each of said temporal electrodes for pivotal movement relative to said band; said arm members being pivotally movable for positioning said temporal electrodes at a plurality of positions relative to said center electrode; and means for affixing said band to the head of a subject so as to position said center electrode substantially centrally upon the forehead of the subject and said temporal electrodes for pivotal movement beneath and to either side of said center electrode, said band comprising a relatively flat member of predetermined thickness over a major portion thereof and having two cross-sectional regions of decreased thickness which extends transversely and continuously across said band, one said continuous region of decreased thickness being disposed on either side of said center electrode to increase the flexibility of the band and facilitate the ability of the band to conform to the contour of the head of a wearer.

2. A system according to claim 1 and further including first electrode-receiving means for mounting said center electrode to said band and second electrode-receiving means for mounting said temporal electrode to said pivotal mounting means; and wherein said pivotal mounting means comprises a pair of similar mounting assemblies, each comprising elongate arm means pivotally mounted at a central portion thereof to said flexible band and having said second electrode-receiving means at one end thereof.

3. A system according to claim 2 wherein said pivotal mounting means are located to either side of said center electrode and substantially equally distant therefrom.

4. A system according to claim 2 wherein each of said first and second electrode-receiving means comprises a hollow cup-like member receiving said electrode therein, the first electrode-receiving means being formed integrally with the band and one second electrode means being formed integrally with each of said elongate arm means.

5. Apparatus according to claim 4 wherein each said electrode comprises a flat, disc-like electrode portion and a connector portion projecting therefrom; and wherein said cup-like member includes a through aperture for receiving said connector portion therethrough.

6. A system according to claim 5 wherein said connector portion comprises a snap-like member having a leading first snap surface projecting through said through aperture of said cup-like member for snappingly engaging a mating connector, and a second, following snap surface snappingly engaging about said through aperture.

7. A system according to claim 5 and further including a gel-filled pad received in said cup-like member and overlying said disc-like electrode portion.

8. A system according to claim 7 and further including removable cover means for overlying and engaging said cup-like member and thereby covering said gel-filled pad received therein.

9. A system according to claim 2 and further including gripping means at an end opposite said one end of said arm means for manually pivoting said arm means.

10. A system according to claim 9 wherein said gripping means extends laterally outwardly of said opposite end of said arm means.

11. A system according to claim 2 wherein each said mounting assembly comprises a one-piece, integrally formed member of a flexible material.

12. A system according to claim 2 wherein said band and said electrode-receiving means thereof comprise a one-piece, integrally formed member of a flexible material.

13. A system according to claim 1 and further including detent means for defining a plurality of detent positions of said pivotal mounting means relative to said band.

14. A system according to claim 13 wherein said pivotal mounting means comprises a pair of similar mounting assemblies, each comprising elongate arm means pivotally mounted at a central portion thereof to said flexible band.

15. A system according to claim 14 wherein said pivot mounting means defines a pivot center, wherein said elongate arm means and said band include substantially flat facing surfaces, and wherein said detent means comprises at least one first raised rib on one of said facing surfaces and lying generally along a radius from said pivot center, and a plurality of spaced apart second ribs on the other of said facing surfaces in a generally arcuate configuration for clicking engagement with said first rib.

16. A system according to claim 15 wherein said detent means further includes a pair of similar first ribs extending oppositely outwardly along a common diameter of said pivot center and wherein said second ribs comprise two groups of ribs substantially symmetrically formed with respect to said pivot center, each said group comprising a plurality of spaced apart ribs, each rib thereof defining a radius from said pivot center.

* * * * *